United States Patent
Vorm

(10) Patent No.: US 9,459,240 B2
(45) Date of Patent: Oct. 4, 2016

(54) INTEGRATED SYSTEM FOR LIQUID SEPARATION AND ELECTROSPRAY IONIZATION

(71) Applicant: Proxeon Biosystems A/S, Odense C (DK)

(72) Inventor: Ole Vorm, Odense M (DK)

(73) Assignee: PROXEON BIOSYSTEMS A/S, Odense C (DK)

( * ) Notice: Subject to any disclaimer, the term of this patent is extended or adjusted under 35 U.S.C. 154(b) by 97 days.

(21) Appl. No.: 14/116,962

(22) PCT Filed: May 3, 2013

(86) PCT No.: PCT/DK2013/050127
§ 371 (c)(1),
(2) Date: Nov. 11, 2013

(87) PCT Pub. No.: WO2013/167131
PCT Pub. Date: Nov. 14, 2013

(65) Prior Publication Data
US 2015/0198571 A1 Jul. 16, 2015

Related U.S. Application Data

(60) Provisional application No. 61/644,498, filed on May 9, 2012.

(30) Foreign Application Priority Data

May 9, 2012 (DK) .................................. 2012 00326

(51) Int. Cl.
*G01N 30/72* (2006.01)
*H01J 49/16* (2006.01)

(52) U.S. Cl.
CPC ......... *G01N 30/7266* (2013.01); *H01J 49/165* (2013.01)

(58) Field of Classification Search
CPC ........................ G01N 30/7266; H01J 49/165
See application file for complete search history.

(56) References Cited

U.S. PATENT DOCUMENTS

| 2008/0038152 A1 | 2/2008 | Van Pelt | 285/284 |
| 2014/0047905 A1* | 2/2014 | Tomany | B05B 5/0255 73/61.52 |
| 2014/0305801 A1* | 10/2014 | Peterson | H01J 49/022 204/604 |

FOREIGN PATENT DOCUMENTS

| CN | 102347199 | 2/2012 |
| GB | 2467826 | 8/2010 |

(Continued)

OTHER PUBLICATIONS

International Search Report from International Application No. PCT/DK2013/050127 mailed Jul. 15, 2013.

*Primary Examiner* — Daniel S Larkin
(74) *Attorney, Agent, or Firm* — Merchant & Gould P.C.

(57) ABSTRACT

The present invention relates to an integrated system for liquid separation, such as LC, CE, affinity chromatography, and ion exchange chromatography. A preferred aspect relates to a specialized protection means for protecting the fragile electrospray needle when not in use. Another preferred aspect relates to a specialized electrical contact means for applying voltage to the electrospray needle. The invention comprises an integrated system for liquid separation and electrospray ionization comprising: a separation column; and an electrospray emitter connected with the separation column. In one aspect there is a retractable protective sleeve (8) for covering and supporting the electrospray emitter (2) along at least a portion of its axis. In another aspect there is an electrically conducting sheath surrounding the emitter and providing an electrical connection.

20 Claims, 4 Drawing Sheets

(56) References Cited

FOREIGN PATENT DOCUMENTS

| WO | WO 98/42007 | 9/1998 |
| WO | WO 03/034464 | 4/2003 |
| WO | WO 2009/147001 | 12/2009 |
| WO | WO 2010/102194 | 9/2010 |
| WO | WO 2010/138678 | 12/2010 |
| WO | WO 2012/139586 | 10/2012 |
| WO | WO 2013/063502 | 5/2013 |

* cited by examiner

INTEGRATED SYSTEM FOR LIQUID SEPARATION AND ELECTROSPRAY IONIZATION

This application is a National Stage Application of PCT/DK2013/050127, filed 3 May 2013, which claims benefit of Serial No. PA 2012 00326, filed 9 May 2012 in Denmark and 61/644,498 filed 9 May 2012 in the United States and which applications are incorporated herein by reference. To the extent appropriate, a claim of priority is made to each of the above disclosed applications.

FIELD OF THE INVENTION

The present invention relates to an integrated system for liquid separation, such as LC, CE, affinity chromatography, and ion exchange chromatography, and electrospray ionization. A preferred aspect relates to a specialised protection means for protecting the fragile electrospray needle when not in use. Another preferred aspect relates to a specialised electrical contact means for applying voltage to the electrospray needle.

BACKGROUND OF THE INVENTION

Proteomics, being the study of protein structure and function, is a research focus for decades to come as it can allow one to elucidate the fundamentals of life and the molecular basis of health and disease. Analysis of complex protein mixtures usually involves two steps: molecular separation and identification/characterization. The method of choice for protein identification and characterization is mass spectrometry (MS) where the analytes of interest are ionized by electrospray ionization (ESI) or matrix-assisted laser desorption/ionization (MALDI). Two separation methods are dominating in the field of proteomics: 2-dimensional gel-electrophoresis (2D-GE) and high-performance liquid chromatography (HPLC). An important advantage of HPLC compared to 2D-GE is its relatively simple coupling to MS through ESI.

One of the demands of the fast growing proteomic research area is a miniaturization of bioanalytical techniques, see e.g. T. Laurell and G. Marko-Varga, "Miniaturization is mandatory unraveling the human proteome", Proteomics, (2002), Vol. 2, pp. 345-351, Lion, N.; Rohner, T. C.; Dayon, L.; Arnaud, I. L.; Damoc, E.; Yonhnovski, N.; Wu, Z. Y.; Roussel, C.; Josserand, J.; Jensen, H.; Rossier, J. S.; Przybylski, M.; Girault, H. H. Electrophoresis 2003, 24, 3533-3562. The miniaturization in liquid chromatography is evidenced by the increasing use of smaller beads, smaller diameter columns, and correspondingly smaller flow rates. Under laboratory conditions miniaturization has led to higher resolution, increased sensitivity, and faster separation.

Another of the demands is the elimination of user intervention with the bioanalytical techniques in order to ensure reproducible results. In this respect, a commercially available microfluidic chip manufactured by Agilent Technologies, Inc. integrates a trapping column, a separation column and an electrospray source (i.e. the emitter) within a single structure, see e.g. Gottschlich, N.; Jacobson, S. C.; Culbertson, C. T.; Ramsey, J. M. Anal Chem 2001, 73, 2669-2674; Fortier, M. H.; Bonneil, E.; Goodley, P.; Thibault, P. Anal Chem 2005, 77, 1631-1640. Meanwhile this system is based on microfluidic chip technology, which is still not a fully matured technology. And whereas this technology provides many user friendly simplifications, the chromatographic performance is currently not able to match that of non-chip based systems.

While conventional HPLC columns (i.e. columns with fittings for connecting to conventional instruments) for use with nano-liter flow rates (also referred to as nano-LC) show superior performance relative to chip-based LC, the problem with incorrect assembly of fittings and fluid connections often compromises the advantages associated with conventional nano-LC columns. In other words, incorrect connections of LC transfer tubing to the LC columns may result in leaks and consequently poor sensitivity and chromatographic separation. Also, incorrect connection of a conventional nano-electrospray emitter after the LC column may give rise to undesired dead-volumes which also leads to reduced sensitivity and poor separating power.

Thus, the integration of a complete LC-ESI system, wherein conventional LC columns and spray emitters are used, and wherein the end-user should not establish the correct fluid connections (correct assembling of fittings), is highly desirable.

The columns and transfer lines ordinarily used in liquid chromatography systems that employ flow rates less than 10 μL/minute most frequently have very narrow inner diameters as well as outer diameters. Consequently, such transfer lines and columns may be physically fragile. Thus it is also highly desirable to provide some means of mechanical relief from strain, pressure, bends, twists etc. such that the thin tubing components are protected and become robust enough to withstand use in everyday laboratory work.

The commonly used interface between chromatography and mass spectrometry is made up by the electrospray ion-source. In the ion source, the eluate from the LC column is passed through an emitter (also termed a needle) that is held at an electric potential that usually differs by one or more kilovolts from an opposing inlet orifice of the mass spectrometer. This enables the eluate, and subsequently the analytes, to adopt electric charges (i.e. become ionized) such that the ionized analytes may be analyzed in the mass spectrometer. The high electric potential differences present a safety hazard if the charged areas can be touched by the operator. Thus it is highly desirable to efficiently shield as many components as possible that are at the elevated potential. The electrospray emitter is a thin fragile component that is potentially easy to damage if not handled carefully and moreover is spiky such that injury can be caused by it. It is therefore desirable to reduce the risk of damage to the electrospray emitter and/or injury by exposure to it.

US 2008/0038152 describes a system where a separation column, connection fittings and a spray emitter are encased in a single package. The end of the spray emitter may be temporarily covered by a retractable sleeve structure to protect the device until installation and operation of the system. The retractable sleeve is slidably mounted around the electrospray emitter, being moveable to an extended position to protect the spray tip. However, the sleeve is freely slideable back and forth and thus inadvertent exposure of the emitter can occur.

In the art of electrospray ionization interfaces there is a need for higher security protection for the tip while not in use.

SUMMARY OF THE INVENTION

The present invention overcomes the problem of inadvertent exposure of the emitter by providing in a first aspect an integrated system for liquid separation and electrospray ionization comprising:

a separation column;

an electrospray emitter connected with the separation column; and a protective sleeve for covering and/or supporting the electrospray emitter along at least a portion of its axis.

The present invention in a second aspect provides an integrated system for liquid separation and electrospray ionization comprising:

a separation column;

an electrospray emitter connected with the separation column; and an electrically conductive sheath surrounding the emitter and providing an electrical connection.

The present invention in a third aspect provides an integrated system for liquid separation and electrospray ionization comprising:

a coiled separation column;

an electrospray emitter connected with the separation column;

heating/cooling means placed around the coiled separation column for controlling the temperature of the separation column;

said separation column, electrospray emitter, and heating/cooling means being embedded in a plastic material. The use of a coiled column makes the column compact and able to fit into a small volume that may more easily be temperature controlled by a heating element than if it were laid straight and would occupy an elongated, typically long, space.

It will be appreciated that the first, second, and third aspects of the invention may be used separately or in combination. In such combined embodiments, preferably the electrically conductive sheath is arranged enclosing the protective sleeve. More preferably, the protective sleeve is movable inside the electrically conductive sheath as hereafter described in more detail.

In some embodiments, the protective sleeve is fixed with respect to the emitter. However, the protective sleeve is most preferably retractable, i.e. with respect to the emitter. Where the sleeve is retractable, this ensures that the emitter tip is exposed when in use and thereby the sleeve does not interfere, for example, with gas flows and equipotential lines around the emitter tip. Moreover, a retractable sleeve, when in use, does not block visibility of the emitter so one can readily monitor the spray. The protective sleeve is preferably slidably located on the emitter. The protective sleeve is preferably movable between an extended (or cover) position wherein it covers the emitter, especially the tip thereof, and a retracted position wherein the emitter, especially the tip thereof, is exposed. When the emitter is exposed it may be used for electrospray ionization. The emitter tip herein means the tip from which ions are produced when in use. The protective sleeve thus covers and supports the electrospray emitter along at least a portion of its axis which includes the tip of the emitter.

The protective sleeve preferably comprises a generally cylindrical body that surrounds, and more preferably supports, the emitter, i.e. when it is slidably mounted thereon. The generally cylindrical body preferably comprises a base of greater diameter than a remainder or main body of the sleeve.

Preferably, a resilient member, more preferably a spring, is provided, e.g. in contact with the protective sleeve, to bias the sleeve towards its extended position. The resilient member is preferably in contact with a base of the protective sleeve. The resilient member is preferably positioned between the separation column and the protective sleeve. In this way, the resilient member, upon activation, is able to force the sleeve to cover the emitter when it is required to be protected. The resilient member also allows the sleeve to be retracted from the tip end of the emitter when the emitter is required to be used, e.g. when the integrated system is assembled with an instrument for mass spectrometric analysis. To enable this retraction, preferably the resilient member is forced into a compressed state, e.g. by pushing the sleeve towards the resilient member. The resilient member biases the sleeve to the extended position such that the sleeve adopts the extended or cover position when the sleeve does not have a sufficient force applied pushing it against the resilient member. The resilient member or spring thereby enables the protective sleeve to cover the tip end of the emitter when the emitter is not required to be used, e.g. when the integrated system is disassembled from an instrument for mass spectrometric analysis.

The protective sleeve is preferably enclosed within an outer sheath, which in preferred aspects of the invention is the electrically conductive sheath described herein. The outer sheath is preferably fixed in position in relation to the emitter. The protective sleeve is preferably capable of reciprocating motion within the outer sheath, thereby enabling the protective sleeve to be retractable with respect to the emitter. In such embodiments, the resilient member such as a spring is also preferably provided inside the outer sheath for providing a force against the sleeve, more preferably against the base of the sleeve, to bias the sleeve towards the extended position.

Thus, in embodiments where the protective sleeve is used in combination with the electrically conductive sheath, preferably the resilient member is provided inside the electrically conductive sheath between the separation column and the protective sleeve covering, whereby the spring, upon activation, is able to force the sleeve out of the sheath to cover the emitter. Thus, in certain preferred embodiments, the protective sleeve may be forced out as soon as the system is pulled out of a recipient holder (as described in more detail below), i.e. the spring force is constantly acting so as to push the sleeve in an outwards direction thereby to cover the emitter.

The protective sleeve is desirably made of a rigid material, such as a metal or polymer material. In this way the rigidity of the sleeve can protect the fragile emitter that it covers.

Preferably, the separation column is embedded in a plastic material. Preferably the electrospray emitter, meaning at least a part thereof, is embedded in a plastic material. By embedding in the plastic material, the integrated system of the present invention may be formed as a cartridge fitting an instrument for mass spectrometric analysis.

Preferably, the separation column is connected directly or via a transferring conduit with the electrospray emitter through one or more end fitting. In preferred embodiments, said separation column and end fittings are embedded in a plastic material. In certain preferred embodiments, said separation column, end fittings and electrospray emitter are embedded in a plastic material. Thus, the integrated system is preferably at least partly embedded in plastic material. In this way, the integrated construction requires less fluidic connections to be made by a user and the connections and end fittings cannot be tampered with, thus reducing the risk of leaks. Instead the embedded connections become the responsibility of the manufacturer. The overall design may therefore be made as a convenient "plug-and-spray" type, which the user only has to fit into a receiving frame or holder on an instrument, e.g. for mass spectrometry. Suitable embedded designs and methods for the manufacture thereof are described in the applicant's earlier patent application WO 2009/147001, the contents of which is hereby incorporated by reference in its entirety.

Preferably, the separation column is an LC column, e.g. HPLC column. The LC column may be used with various flow rates, e.g. down to as low as nano-LC flow rates, i.e. 100 nL/min or less.

Preferably, the separation column, meaning at least part thereof, is coiled, i.e. rolled up in a loop. This feature enables space saving since it allows a column to take up less space than if it were laid straight and it permits different column lengths to be used in the same design of integrated system, i.e. by changing the number of windings in the coil. This feature further makes the column compact and able to fit into a small volume that may more easily be temperature controlled by a heating element than if it were laid straight and would occupy an elongated, typically long, space.

Preferably, the electrospray emitter comprises an electrically conductive capillary, such as a metal capillary or a glass capillary, e.g. glass coated with electrically conductive material. However, glass capillaries that are not conductive or coated may be used.

The electrically conductive sheath provides an electrical connection to enable the emitter to receive a high voltage. The sheath may provide an electrical connection to the emitter either directly or via one or more intermediate electrically conductive bodies, e.g. the protective sleeve or the fitting that connects the emitter to the column or a conduit. In a preferred arrangement, the electrically conductive sheath encloses and electrically contacts the protective sleeve and the sleeve electrically contacts the emitter. In another preferred arrangement, the electrically conductive sheath encloses and electrically contacts the fitting that connects the emitter to the upstream column (or conduit) and the fitting electrically contacts the electrically conductive liquid (eluent) at the point of entering the emitter, thereby enabling the transfer of charge from the high voltage contact point to the tip of the emitter.

Preferably, the electrically conductive sheath is enclosed within a holder having a high-voltage contact point when the integrated system is in use. The holder is preferably a holder located on an instrument, e.g. for mass spectrometric analysis.

Preferably, the high-voltage contact point is an electrically conductive ball fitting a recess, such as a groove, in the outer surface of the electrically conductive sheath. The groove is preferably a circumferential groove in the outer surface of the electrically conductive sheath. The contact point may be, for example, a spring loaded ball bearing.

The electrically conductive sheath preferably has a shape that provides a close or tight fit in a receiving holder on a laboratory apparatus (e.g. mass spectrometer). In a specific embodiment, the electrically conductive sheath preferably has a cylindrical, i.e. circular cylindrical, outer shape. Preferably, in that case, the holder has a cylindrical, i.e. circular cylindrical, receiving space, to receive the electrically conductive sheath of the integrated system. In this way, with such cylindrical shaped parts and a groove (preferably circumferential) in the outer surface of the electrically conductive sheath to receive the high voltage contact point, an exact angular alignment of the integrated system in the holder is not essential. An axial alignment of the integrated system (and thereby the emitter) in the holder can be achieved by means of providing an appropriate stop within the holder and/or by means of the contact point fitting in the groove in the outer surface of the electrically conductive sheath.

In manufacturing the integrated system of the present invention, plastifying the plastic material that is used for embedding the integrated system may be achieved in various ways, preferably by heating the plastic material beyond the softening temperature for bringing it in its softening range and making it soft. In a preferred embodiment the entire column and fittings are surrounded by the plastic material. The plastic material may be provided as a plastic molding part. The molding part may be a pre-formed part adapted to the shape of the integrated separation column and of the forming tool.

The forming of the molding part may be achieved by closing the forming tool and exerting pressure on the pre-formed part. Alternatively, this is achieved by closing the forming tool and heating the forming tool together with the plastic material.

In preferred embodiments of the present invention the forming of the molded part may be achieved by injecting molten plastic material into a mold wherein the LC column with fittings and other related or required components are located and allowing the molten plastic to embed these parts and cool off and harden to become solid. Alternatively the molded part may be shaped by exerting pressure on the plastic material caused by the thermal expansion of the plastic material by heating the closed forming tool comprising the plastic material, alternatively by exerting pressure on the plastic material by closing the forming tool, or actively cooling down the plastic material and/or the forming tool. Still another alternative embodiment may be achieved by mixing chemicals that subsequently polymerize inside a mold thereby embedding the LC column with fittings and other related components such as the emitter.

The plastic material used in the method of the present invention may be thermoplastic material or thermosetting material. Preferably, the plastic material is at least one of: a thermoplastic material, polyetheretherketone (PEEK), one of a broad range of fluoropolymers, in particular perfluoro-amines (PFA) or fluorinated ethylene-propylene copolymer (FEP), duroplastic material or compound, in particular polyimide, and liquid crystal polymers (LCP).

Preferably, the plastic materials of the present invention are thermoplastic hotmelts based on polyamide, such as those marketed under the tradename MacroMelt (Henkel Kommanditgesellschaft). These includes at least one room-temperature-flowable polymerizable compound in combination with a polymeric matrix present in an amount sufficient to render the composition non-flowable at temperatures of at least about 49° C. The polymerizable compound or composition may be selected from a wide group of materials including anaerobics, epoxies, acrylics, polyurethanes, olefinic compounds and combinations thereof. Anaerobic compositions are most desirable since they have unique applications in many threadlocking and sealant areas where the need for a non-flowable material exists. The polymeric matrix may be selected from polyamides, polyacrylamides, polyimides, polyhydroxyalkylacrylates and combinations thereof. In one desired embodiment of the present invention an anaerobic adhesive composition is provided which includes a polymerizable (meth) acrylate monomer, a polymerization initiator for the monomer, and a polymeric matrix material miscible or otherwise compatible with the monomer. The matrix material is present in an amount sufficient to render the composition non-flowable at temperatures of at least about 210° C. The polymeric matrix and polymerizable component readily form a stable mixture or combination without phase separation of component parts.

In order to meet the most relevant requirements in relation to the operation of the column, the integrated separation column may be equipped with one or more embedded components of: a heating and/or cooling element and a thermal sensor in close proximity or contact with the column and preferably embedded in the plastic material.

For optimum performance, channels for gas flow may also be embedded in the plastic material; the outlet of these channels being in close proximity with the apex (tip) of the emitter, whereby gas leaving the outlet assists in the desolvation of the spray cloud.

In order to facilitate identification of the integrated column, the embedded components may further comprise an identification tag, such as a radio frequency identification tag (RFID) embedded in the plastic material.

In order to ensure correct positioning of the integrated system of column and electrospray emitter relative to e.g. the MS inlet, the present invention also provides a holder adapted for receiving the integrated system.

It is important to emphasize that preferred embodiments of the present invention are also directed to an integrated separation column comprising end fittings embedded in a plastic material, irrespective of the method used for the embedment in the plastic material. Also, in this general embodiment the integrated separation column may further comprise an electrospray emitter directly connected with the separation column through one of the end fittings. Moreover, as in the other embodiments of the present invention the plastic material is at least one of: a thermoplastic material, preferably based on polyamide and/or polyurethane, polyetheretherketone (PEEK), one of a broad range of fluoropolymers, in particular perfluoroamines (PFA) or fluorinated ethylene-propylene copolymer (FEP), duroplastic material or compound, in particular polyimide, liquid crystal polymers (LCP). Finally, the integrated separation column may in agreement with the other described embodiments of the present invention further comprise one or more of: an RFID-tag, heating/cooling elements and thermo sensor, a high-voltage contact point for the electrospray emitter, counter electrode(s) with a geometry that benefits definition of the field lines around the electrospray emitter, and channels for gas flow embedded in the plastic material.

Coupling with a laboratory apparatus, for example a mass spectrometer, becomes easier. Additionally an exact and repeatable positioning process of the integrated column relatively to the frame can be guaranteed by molding the plastic material to a shape that provides a close or tight fit in a receiving holder on the laboratory apparatus. The ease and accuracy of the positioning may be further enhanced by use of shapes that by design help lock the two items into a given position (e.g. by way of convex/concave mating surfaces, magnets or spring loads). This also enables the exact positioning of the integrated column into a laboratory apparatus if the holder is positioned precisely in the laboratory apparatus.

In addition to shielding the column, emitter and fittings from disassembly (whether intentional or accidental), the plastic embedding also renders physical strength to some otherwise rather fragile components that are prone to be damaged through everyday usage in laboratory environments. Nano-LC columns are frequently and advantageously made from a piece of silica glass tubing where said tubing typically is 10 mm to 1000 mm long but has an outer diameter of around 300 µm and hence the tubing can easily break. Typically such silica glass tubing has an outer polymer lining of a few micrometers thickness that renders some strength but the glass tubing is still easily broken. Similarly the emitter is made from a very narrow piece of metal or glass tubing and can readily be damaged by contact with other items. The plastic embedding described herein makes the integrated column robust and durable such that they cannot readily break by accident. The protection of the column and emitter includes protection from physical strains, twists, bends as well as the pressure of the liquid inside the tubing whose thin walls are made several fold thicker by the plastic matrix being in direct (chemical) contact with the outer surface of the tubing.

The chromatographic retention times that are observed for the individual analytes are highly dependent on the temperature at which the separation takes place. Slight variation in temperature can lead to pronounced shifts in retention times and in order to obtain reproducible data, it is often sought to maintain stable ambient temperatures for the column. NanoLC columns—by virtue of their small diameters—can readily exchange heat with the surrounding air. This is however prevented by the plastic matrix which provides thermal insulation of the columns and therefore assists in maintaining stable column temperatures.

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

For the sake of completeness the present disclosure distinguishes between the first (A), second (B), and third (C) aspects in accordance with the following schemes.

Aspect A

1A. An integrated system for liquid separation and electrospray ionization comprising:
   a separation column (1);
   an electrospray emitter (2) connected with the separation column (1); and
   a retractable protective sleeve (8) for covering and supporting the electrospray emitter (2) along at least a portion of its axis.

2A. The integrated system according to aspect 1A wherein the retractable protective sleeve (8) is slidably mounted around the electrospray emitter.

3A. The integrated system according to aspect 1A or 2A, wherein the retractable protective sleeve (8) is moveable to an extended position wherein a tip of the electrospray emitter is covered by the protective sleeve.

4A. The integrated system according to aspect 3A, wherein a resilient member (10) is provided to bias the protective sleeve towards the extended position wherein it covers the tip of the electrospray emitter.

5A. The integrated system according to any preceding aspect A, wherein the retractable protective sleeve is moveable to a retracted position wherein a tip of the electrospray emitter is uncovered.

6A. The integrated system according to any preceding aspect A, wherein the protective sleeve (8) is enclosed within and is moveable within an outer sheath.

7A. The integrated system according to aspect 6, wherein the outer sheath is an electrically conducting sheath.

8A. The integrated system according to any preceding aspect A, wherein the separation column (1) and electrospray emitter (2) are embedded in a plastic material (15).

9A. The integrated system according to any preceding aspect A, wherein the separation column (1) is connected directly or via a transferring conduit with the electrospray emitter (2) through one or more end fittings (3, 4), and said separation column (1), end fittings (3,4) and electrospray emitter (2) are embedded in a plastic material (15).

10A. The integrated system according to any preceding aspect A, wherein the separation column (1) is an LC column.

11A. The integrated system according to any preceding aspect A, wherein the separation column (1) is coiled in a loop.

12A. The integrated system according to any preceding aspect A, wherein the electrospray emitter (2) comprises a metal capillary or a glass capillary.

13A. The integrated system according to aspect 7A, wherein the electrically conductive sheath (7) is adapted for insertion within a holder having a high-voltage contact point.

14A. The integrated system according to aspect 13A, wherein the electrically conductive sheath has a recess to receive the high-voltage contact point.

15A. The integrated system according to aspect 13A or 14A, wherein the high-voltage contact point comprises an electrically conductive ball.

16A. The integrated system according to aspect 15A, wherein the electrically conductive ball (9) fits a groove in the outer surface of the electrically conductive sheath.

17A. The integrated system according to any one of aspects 13A to 16A, wherein the holder is fixed on a mass spectrometer.

Aspect B

1B. An integrated system for liquid separation and electrospray ionization comprising:
a separation column;
an electrospray emitter connected with the separation column; and
an electrically conducting sheath surrounding the emitter and providing an electrical connection.

2B. The integrated system according to aspect 1B wherein the electrically conducting sheath is made of metal.

3B. The integrated system according to aspect 1B or 2B, wherein the electrically conductive sheath is for insertion within a holder having a high-voltage contact point.

4B. The integrated system according to any preceding aspect B, wherein the electrically conductive sheath has a recess to receive a high-voltage contact point.

5B. The integrated system according to aspect 4B, wherein the high-voltage contact point comprises an electrically conductive ball.

6B. The integrated system according to aspect 5B, wherein the electrically conductive ball fits a groove in the outer surface of the electrically conductive sheath.

7B. The integrated system according to aspect 3B, wherein the holder is fixed on a mass spectrometer.

8B. The integrated system according to any preceding aspect B, wherein a retractable protective sleeve is slidably mounted on the electrospray emitter and said electrically conductive sheath encloses said retractable protective sleeve.

9B. The integrated system according to aspect 8B, wherein the retractable protective sleeve is moveable to an extended position wherein a tip of the electrospray emitter is covered by the protective sleeve.

10B. The integrated system according to aspect 8B or 9B, wherein a resilient member is provided to bias the protective sleeve towards the extended position wherein it covers the tip of the electrospray emitter.

11B. The integrated system according to any one of aspects 8B to 10B, wherein the retractable protective sleeve is moveable to a retracted position wherein a tip of the electrospray emitter is uncovered.

12B. The integrated system according to any one of aspects 8B to 11B, wherein the protective sleeve is enclosed within and is moveable within the electrically conductive sheath.

13B. The integrated system according to any preceding aspect B, wherein the separation column and electrospray emitter are embedded in a plastic material.

14B. The integrated system according to any preceding aspect B, wherein the separation column is connected directly or via a transferring conduit with the electrospray emitter through one or more end fittings, and said separation column, end fittings and electrospray emitter are embedded in a plastic material.

15B. The integrated system according to any preceding aspect B, wherein the separation column is an LC column.

16B. The integrated system according to any preceding aspect B, wherein the separation column is coiled in a loop.

17B. The integrated system according to any preceding aspect B, wherein the electrospray emitter comprises a metal capillary or a glass capillary.

Aspect C

1C. An integrated system for liquid separation and electrospray ionization comprising:
a coiled separation column;
an electrospray emitter connected with the separation column;
heating/cooling means placed around the coiled separation column for controlling the temperature of the separation column;
said separation column, electrospray emitter, and heating/cooling means being embedded in a plastic material.

2C. The integrated separation system of aspect 1C, wherein the electrospray emitter is either based on a glass capillary coated with electrically conductive material or a conductive metal, such as stainless steel.

3C. The integrated separation system of aspect 2C, wherein the integrated separation column and electrospray emitter are embedded in the same plastic material.

4C. The integrated separation system of aspect 3C further comprising one of more of: RFID-tag, a high-voltage contact point for the electrospray emitter, counter electrode(s) with a geometry that benefits definition of the field lines around the electrospray emitter, and channels for gas flow embedded in the same plastic material.

5C. The integrated separation system of any one of the aspects 1C to 4C, wherein the plastic material is at least one of: a thermoplastic material, preferably based on polyamide and/or polyurethane, polyetheretherketone (PEEK), one of a broad range of fluoropolymers, in particular perfluoroamines (PFA) or fluorinated ethylene-propylene copolymer (FEP), duroplastic material or compound, in particular polyimide, liquid crystal polymers (LCP).

6C. The integrated separation system of any one of the aspects 1C to 5C, wherein the separation column is coiled in a loop.

DETAILED DESCRIPTION OF THE INVENTION

Figure 1:
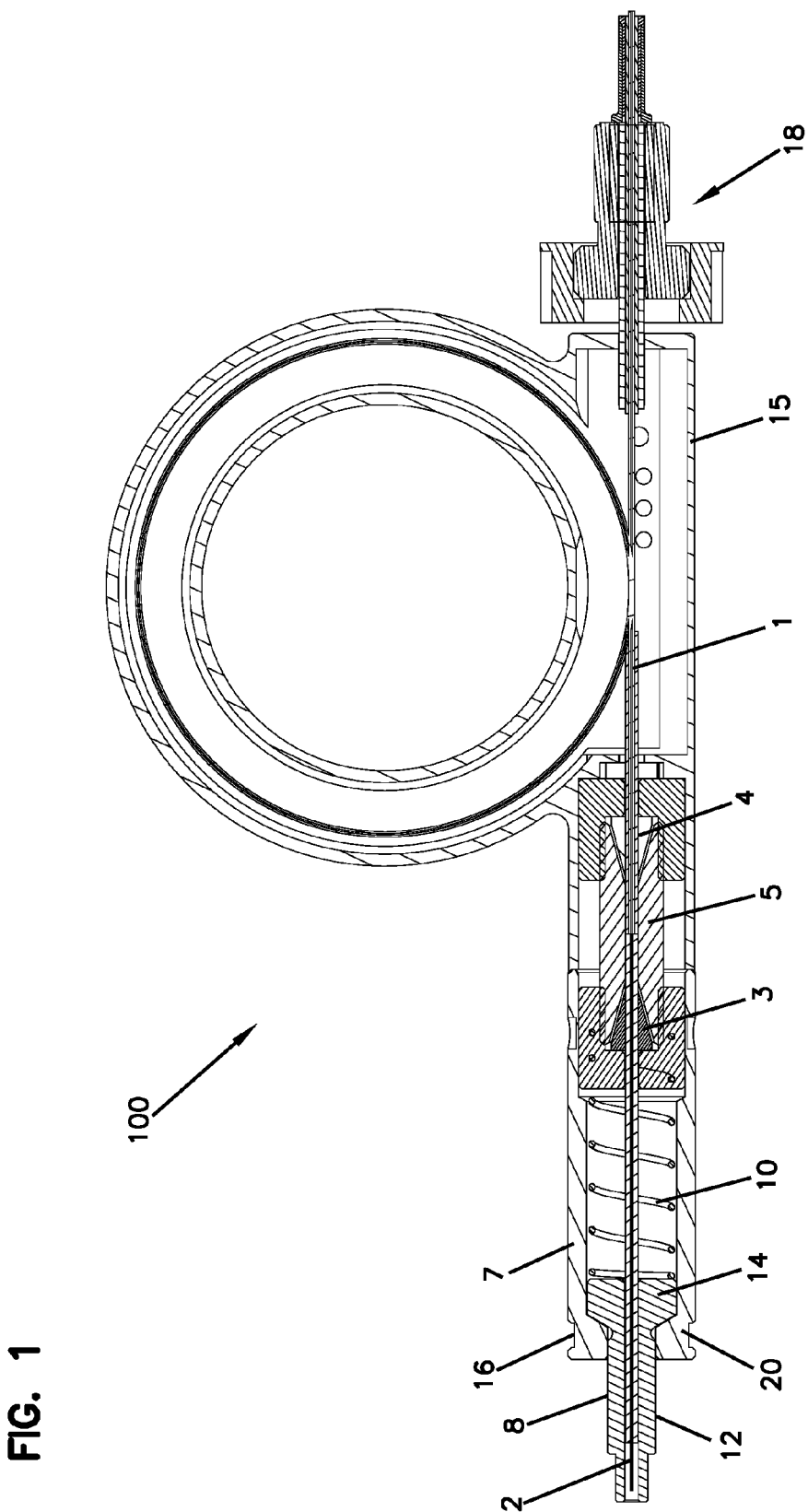
FIG. 1 shows a schematic cross-sectional side view of an integrated system according to the present invention. In this view the protective sleeve is shown covering the electrospray emitter.

The arrangement as shown in FIG. 1 comprises an integrated system (100) comprising a pre-assembled HPLC column (1) connected to the emitter (2) with column fittings (3, 4, 5). The emitter is typically a metal or glass needle or capillary as known in the art. The fittings may be of a conventional type for coupling an LC column to an electrospray emitter. The column (1) is coiled into a loop comprising multiple column windings to increase the separation length. The assembled coiled column, fittings and emitter are embedded in a molding part (15). The molding part (15) comprises a plastic material, for example, a thermoplastic material, for example, polyamide and polyurethane based MacroMelt™. Suitable methods to embed the assembly are described in the applicant's patent application WO 2009/147001. The back end of the column is shown provided with further fittings (18), e.g. for connection to an injector or other HPLC components. This molding provides rigidity to the system, as well as provides a shield against a user disassembling, intentionally or by accident, the fittings and emitter.

A protective sleeve (8) of generally cylindrical form is slidably located on the emitter (2). The sleeve has a main body (12) and a base (14) of wider diameter than the main body. The protective sleeve (8) is typically made of plastic. Mounted about the protective sleeve (8) is an electrically conductive sheath (7), e.g. made of metal. The conductive sheath (7) is supported at one end by one or more of the column fittings. If necessary, the conductive sheath (7) may be detached from the column fittings at that end. The conductive sheath (7) has an internal diameter such as to accommodate therein the protective sleeve (8) and permit the protective sleeve (8) to slidably move in a reciprocating manner inside the sheath as further described below.

A spring (10) is further provided inside the electrically conductive sheath (7), positioned in a space between the column fittings and the protective sleeve (8), thereby to act upon the base of the protective sleeve. In this way, the spring (10), biases the sleeve (8) to force it out of the electrically conductive sheath (7). The length of the sleeve (8) and its extension out of the sheath is sufficient to cover the tip of the emitter (2) and act to protect it against damage. A part of the main body (12) of the protective sleeve (8) protrudes outside the sheath (7) and thereby covers the emitter. The extent of travel of the sleeve (8) out of the sheath (7) is restricted by a reduced internal diameter part (20) at the end of the sheath (7) that stops the wider diameter base (14) of the sleeve. If a force is applied to the sleeve (8) to push the sleeve backwards into the sheath (7), the spring (10) becomes compressed and the tip of the emitter becomes exposed and ready for use as described in more detail below.

The electrically conductive sheath (7) has a recess in the form of a circumferential groove (16) in its outer surface for the purpose of making contact with a high voltage contact, e.g. a contact ball, as described further below.

Figure 2:
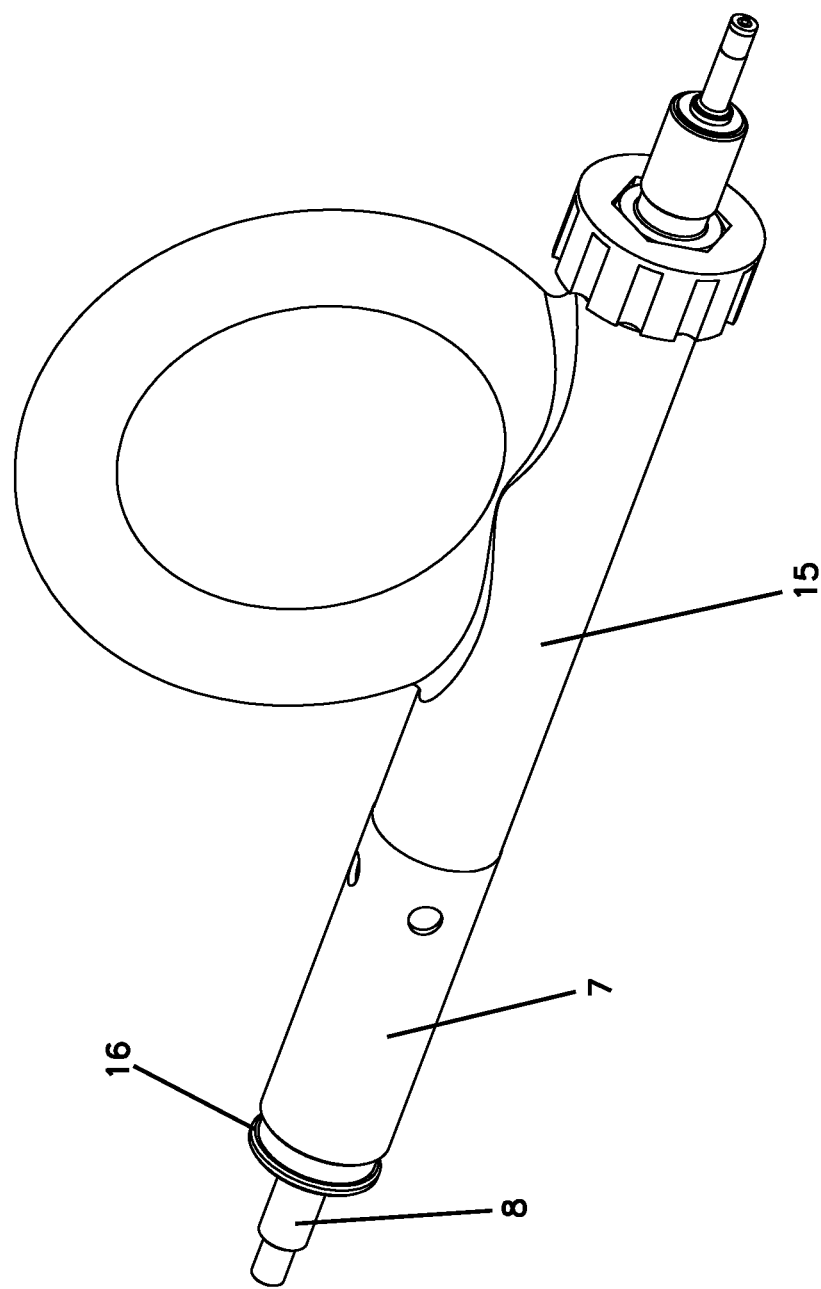
FIG. 2 shows the arrangement of FIG. 1 from the outside.

FIG. 2 shows the arrangement of FIG. 1 from the outside such that the plastic molding (15) is clearly shown covering the integrated system with the electrically conductive sheath (7) mounted at the front end and the protruding sleeve (8) protecting the emitter (not visible). It will be appreciated from the description that the whole integrated system is thus formed as a type of cartridge for use with an instrument, e.g. mass spectrometer.

Figure 3:
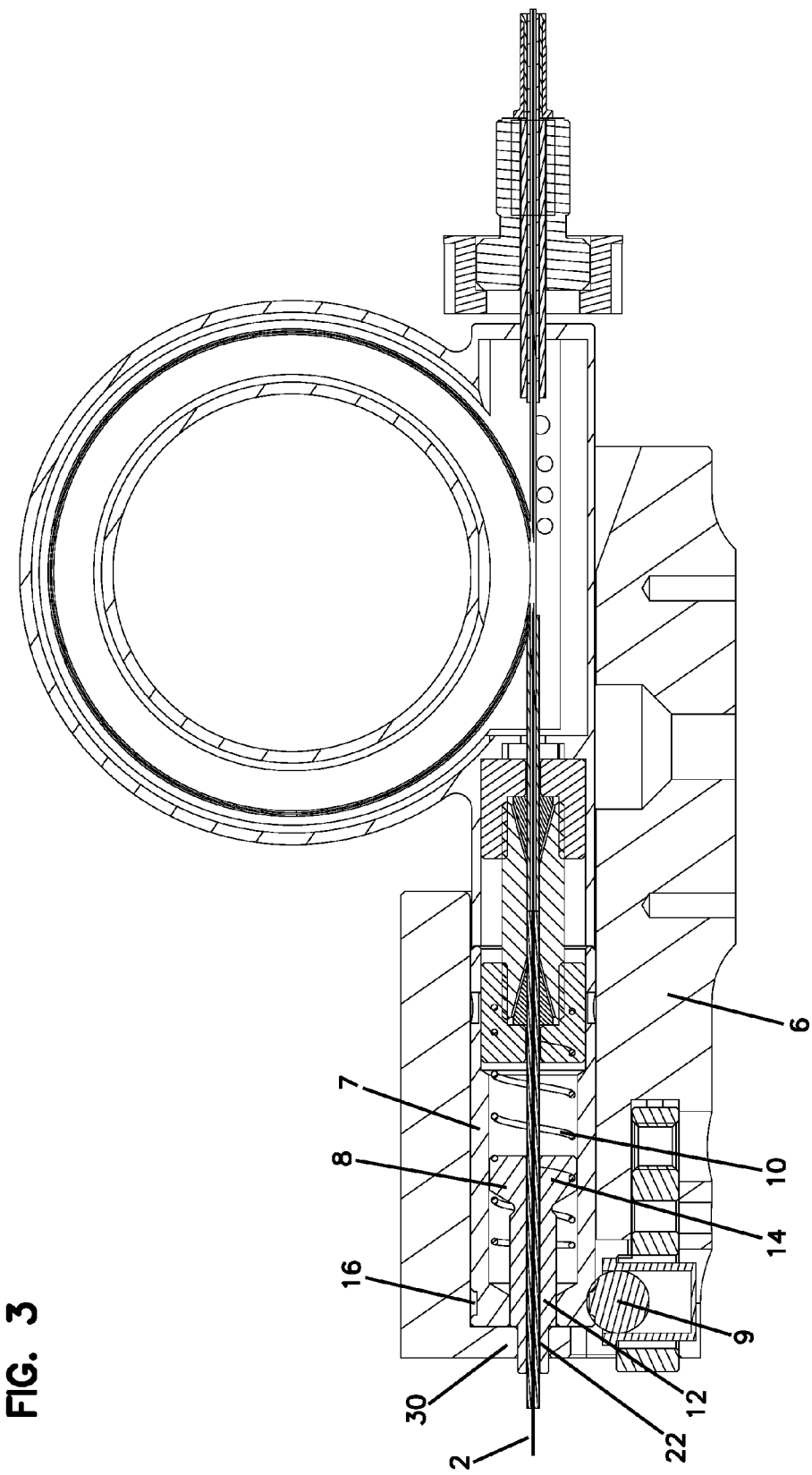
FIG. 3 shows a schematic cross-sectional side view of an integrated system according to the present invention assembled in a holder of a laboratory instrument.

FIG. 3 shows a cross-sectional side view of an integrated system according to the present invention assembled in a holder of a laboratory instrument. As shown in the Figure, a holder (6) (or adapter) is shown that fits to the outer shape of the electrically conductive sheath (7) (that encloses the protective sleeve (8) and provides the electrical connection). The holder (6) may be fixed on a laboratory instrument (e.g. mass spectrometer) that is not shown in the figure. The electrically conductive sheath (7) has an outer shape that provides a close, preferably tight, fit in the receiving holder (6). In this specific embodiment, the electrically conductive sheath (7) has a circular cylindrical outer shape and the holder (6) has a circular cylindrical receiving space to receive the electrically conductive sheath (7).

A ball (9) for the high voltage (HV) connection, which also provides a snap-on connection for the electrically conductive sheath (7), is also shown. The ball (9) is preferably a spring loaded ball bearing that fits the groove (16) in the outer surface of the electrically conductive sheath (7) and provides the HC connection thereto. Axial alignment of the integrated system (and thereby the emitter) in the holder (6) is achieved by means of inserting the electrically conductive sheath (7) of the integrated system into the holder (6) until the HV ball contact (9) fits in the groove (16) in the outer surface of the electrically conductive sheath and snaps or locks the assembly into place within the holder (6). The electrically conductive sheath (7) encloses and electrically contacts the fitting (5) that, along with fittings (3, 4), connects the emitter (2) to the upstream column (1). The fitting electrically contacts the emitter and/or contacts the electrically conductive liquid (eluent) at the point of entering the emitter, thereby enabling the transfer of charge from the high voltage contact point to the tip of the emitter.

The integrated system also permits simultaneous retraction of the protective sleeve (8) from the emitter tip as the integrated system is inserted in the holder (6) to allow the emitter to be used, e.g. in the mass spectrometer. For this purpose, whilst the emitter (2) fits through an orifice (30) in the holder (6), the main body (12) of the sleeve (8) does not. The orifice (30) may lead into an ionisation chamber, e.g. of a mass spectrometer. In fact, in this embodiment, the sleeve (8) has an end portion (22) of reduced diameter compared to its main body (12). In this way, the reduced diameter portion (22) of the protective sleeve fits through the orifice (30) in the holder (6) and may thereby support the emitter in this region. However, the orifice (30) is dimensioned such that it will not allow the main body (12) of the protective sleeve (8) to fit through. In this way, as the integrated system is inserted in to the holder (6), the main body (12) of the protective sleeve (8) pushes against the wall surrounding the orifice (30) and thereby the sleeve (8) is pushed backwards inside the conductive sheath (7), the spring (10) compressing in the process, and the emitter tip becomes exposed for use.

It will be appreciated that when the integrated assembly is withdrawn from the holder (6), the travel of the sleeve (8) will no longer be restricted by the wall surrounding the orifice (30) in the holder (6) such that the spring (10) will force the sleeve (8) out of the sheath (7) once again so as to cover and protect the emitter (2), as shown in FIG. 1.

Figure 4:
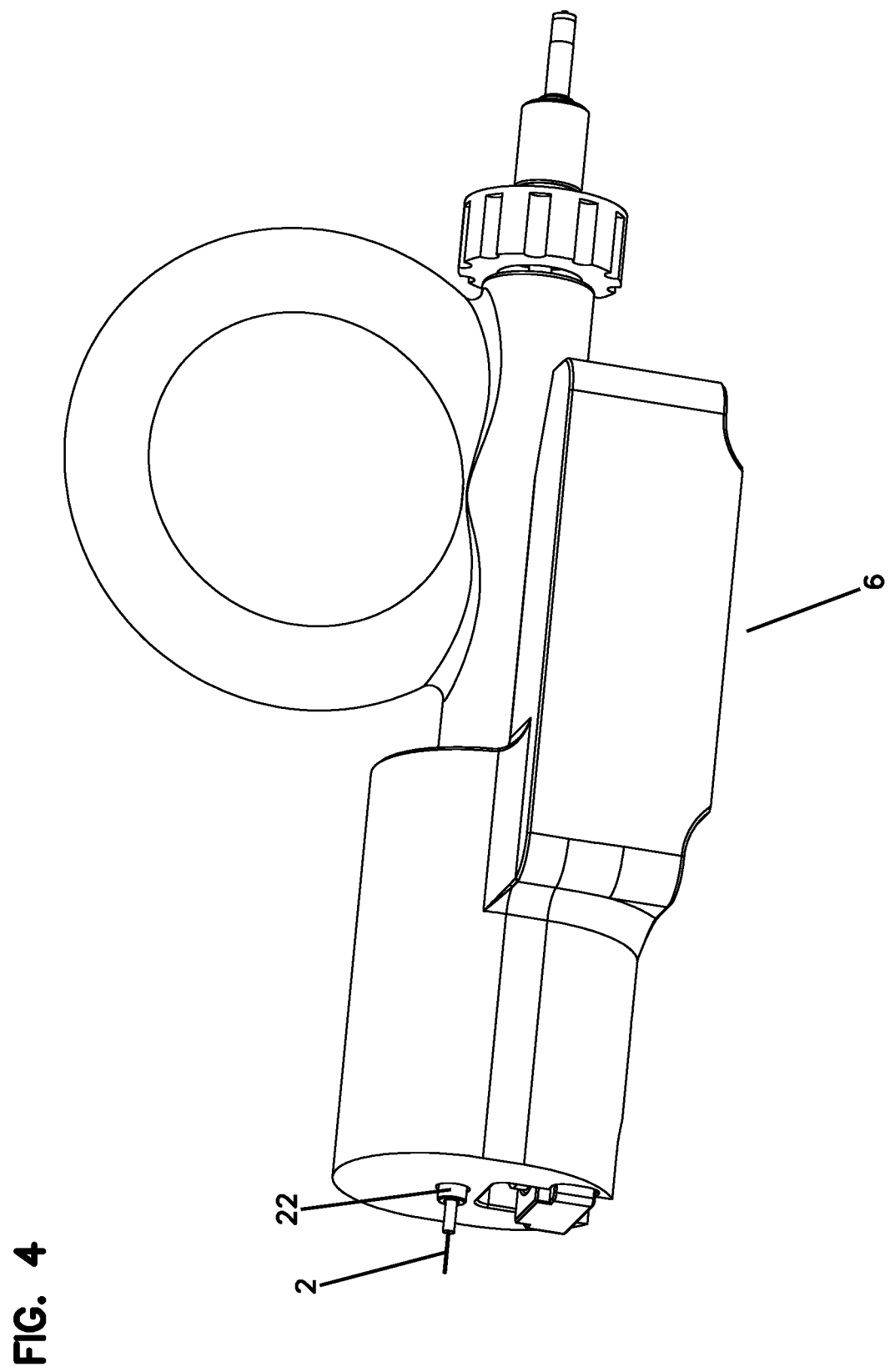
FIG. 4 shows the arrangement of FIG. 3 from the outside.

FIG. 4 shows the arrangement of FIG. 3 from the outside.

According to the present invention, devices and techniques for HPLC applications are provided. More particularly, the invention provides an integrated device for performing separation of compounds. Merely by way of example, the invention has been applied to a high pressure liquid chromatography process.

Embodiments may comprise one or more of the following: a part surrounding an HPLC column with end fittings that are plastified and molded within a forming tool for forming or for shaping the form of the integrated column and for fixing the fittings (e.g. nuts and bolts). The molding part comprises a plastic material. Advantageously, this technique enables sealing and positioning of said fittings and column. Advantageously, the forming tool can form the shape, for example the outer shape, of the integrated column to a desired shape with a good dimensional stability and a high reproducibility. Additionally, close tolerances can be held or maintained, for example, by exactly adjusting the process parameters like the temperature and the detention time within the forming tool.

The molding part can be realized as a pre-formed part, wherein the shape of the pre-formed part is adapted to the shape of the column and fittings and of the forming tool. The pre-formed molding part can be plastified by heating the plastic material above or beyond the softening temperature and bringing it in its softening range for making it soft and pliable. Advantageously, the plastified plastic material can be evenly formed to the outer surfaces of the column and fittings. This enables a homogenous force distribution across the surfaces. Besides this, the mechanical stress after forming can be reduced.

In embodiments, the pre-formed molding part can comprise two or more component parts, wherein said component parts are joined to each other.

Most advantageously, the molding part can be realized by injecting molten plastic material into a mold and allowing this to cool to such temperature where the plastic forms a stable solid which may be flexible or entirely rigid depending on the chosen chemical composition of the plastic material.

In embodiments, the forming tool is equipped at least partly with at least one HPLC column and fittings and with at least one pre-formed part. The pre-formed part comprises the plastic material and is adapted to be formed for producing the sheath around the column and fittings. Advantageously, the pre-formed part can be easily produced with a relative low exactness, for example, by extruding, injection molding or alike and is thus cost effective.

Advantageously, the formed columns fulfill a given set of tolerances. The dimensional consistency is guaranteed by forming the pre-formed molding part or the molten plastic by the forming tool. One forming tool can be used for different insets, different types of conduits, for example, polymer tubing, capillaries, glass capillaries, fused silica capillaries, rods, bars, needles, syringes or alike.

Before forming the molding part around the column and fittings, an outer surface of the column and fittings can be at least partly surrounded with the pre-formed molding part. After forming, the functional element can adhere to the outer surface of the conduit, for example, by frictional forces, shrink forces and/or a chemical bond. For forming the molding part around the column and fittings, the forming tool can be closed for exerting pressure on the softened pre-formed part, or, as the case may be, allow a molten plastic to be injected under pressure.

The tool can be closed and heated together with the plastic material of the pre-formed part. Possibly, pressure can be exerted on the plastic material by thermal expanding the plastic material by heating it within the closed forming tool. Besides this, the pressure can be exerted by a moving piston of the forming tool. After forming, the forming tool can be opened. Possibly, the tool can be opened before cooling down the already formed molding part. By this, the production quantity per time unit can be increased. The step of cooling down the functional element to ambient temperature can be parallelized with the step of forming the next unit. Or, for adjusting, for example, a lower and/or exacter temperature gradient, the plastic material can be cooled down within the forming tool. The cooling step can also be forced actively by well known practices like air cooling, or fluidic cooling of the parts, or surrounding parts, or with a thermocouple.

Advantageously, the plastic material can be shrunk on the outer surface of the column and fittings by cooling the plastic material down to ambient temperature.

Embodiments may comprise one or more of the following. The plastic material can be heated within the forming tool close to or above the melting temperature for bringing the plastic material to the softening range or for melting the plastic material. By this, a chemical bond between the outer surface and the plastic material is possible. For avoiding a similar chemical bond of the plastic material at the boundary point of the inner surface of the mold to the forming tool, one can choose a tooling material which will not cling together with the plastic material or the mold and/or the forming tool can be coated with an according release agent.

The plastic material can be a thermoplastic material or compound, for example polyamide and polyurethane, polyetheretherketone (PEEK), fluoropolymers for example perfluoroamines (PFA) or fluorinated ethylene-propylene copolymer (FEP), duroplastic material or compound for example polyimide, LCP (liquid crystal polymers), and/or perfluoroamines (PFA), comprising advantageous material properties; for example, high persistence against aggressive solvents and good properties for sealing.

Preferably the plastic material comprises molding compounds are thermoplastic hotmelts based on polyamide. The products of the Macromelt® series are exciting not only technically but also ecologically as they are produced from renewable raw materials. No chemical reactions take place during application and no solvents are released. Macromelt® hotmelts are processed at temperatures of 130 to 240° C. and can be used at temperatures from −40 to +140° C. Adhesion to PA, PBT, PVC and similar polar substrates is very good.

Macromelt® hotmelts may be distinguished from other hotmelts by their exceptional mechanical properties. With a high Shore hardness, it produces a plastic-like surface, which is achieved by its high crystalline shares. Macromelt® hotmelts have extremely good mechanical and chemical strength and an excellent adhesion to the materials used to manufacture separation columns, including PEEK, metal, and PVC.

Additionally, the plastic material can be coated after forming with a sealing material, for example, with silicone, rubber, Teflon®, epoxy, or alike.

Further embodiments of the present invention relate to an arrangement of a coupling for bringing conduits in communication. The coupling comprises at least one conduit adapted for conducting a medium, for example, an HPLC column, and an element, such as a fitting with ferules, adapted for bringing the conduit in communication with another conduit, for example, an electrospray emitter or needle.

In an alternative embodiment of the present invention only the fittings and/or minor parts of the conduits are embedded in the molding material in order to prevent the disassembly of the arrangement and shield from the electric HV potential, whereas; in this embodiment the actual conduits, which may be the column body or a transfer line, may be so long as to be impractical or impossible to include in the embedded volume in their entirety.

Column Dimensions

The chromatography columns of the present invention may have a variety of sizes depending on the use of the chromatography column. For example, chromatography columns of the present invention may have any height (also referred to herein as the column length), although columns almost invariably have an overall height of less than 3 meters (m) and usually less than 1 meter and typically a height around 10 cm. In some embodiments, chromatography columns of the present invention have a height (or length) ranging from about 0.50 mm to about 1.0 m.

Chromatography columns of the present invention may also have a tubular wall structure of an overall thickness that varies, depending on the requirements of the column (e.g., the pressure capacity). Typically, chromatography columns of the present invention have a tubular wall structure overall thickness of up to about 50 mm. In some embodiments, chromatography columns of the present invention have a tubular wall structure overall thickness ranging from about 25 µm to about 10 mm.

Chromatography columns of the present invention may be constructed from the above-referenced materials in order to withstand an internal pressure that varies depending on the end use of a given column. Typically, chromatography columns of the present invention are constructed to have a pressure capacity of up to about 50,000 psig. In some embodiments, chromatography columns of the present invention are constructed to have a pressure capacity ranging from about 500 to about 50,000 psig.

Fittings

Fittings as used for the present invention may be any fittings known in the art for LC. The fittings may be constructed from a wide range of polymer materials where often a hard and chemically inert polymer such as PEEK is preferred. Alternatively fittings may be made of a range of metals where stainless steel and titanium usually are the preferred materials. For the purpose of making electrical contact between an electrospray emitter and the power supply that supplies the electrospray potential as described herein, it is advantageous that the fitting materials be conductive, which means metal is usually the material of choice.

Fittings may include ferrules or gaskets that provide a seal between the body of fitting and the conduits that are to be connected. The build-up of dead-volumes or un-swept volumes inside the conduits and fittings is best avoided by butt-connecting all conduits, which leads to the best chromatographic performance. Despite the foregoing, conduits that are joined inside the fittings, may still be kept apart by small distances made up by the thickness of filter-disks, metal grids, or similar without noticeable deterioration of the chromatographic resolving power of the integrated unit.

Electrospray Emitter

The electrospray emitter as used for the present invention may be of any construction known in the art. The electrospray emitter may be made of glass tubing which may end in a sharp or a blunt tip. It is usually preferable to have a sharp and tapered tip such as that obtained when using an automated capillary puller (e.g. from Sutter Instrument, Inc., Novato, Calif., USA) since such emitters provide a more stable spray than blunt emitters do. Typically such tapered emitters have an outer diameter of about 360 µm and an inner diameter of 5 µm to 100 µm whereas the orifice at the tapered tip is usually around 1 µm to 15 µm. The length of such emitters is usually between 30 mm and 60 mm but may also be longer or shorter.

Still better performance is usually obtained from emitters that are made of a conductive material, hereunder steel, and bi-modal materials such as gold and nickel. Some embodiments of the present invention preferably use stainless steel emitters than have an outer diameter between 100 µm and 500 µm and an inner diameter between 5 µm and 100 µm.

Excellent performance is also obtained from emitters that are made of fused silica glass that has been mechanically polished on the outer surface to form a sharp tip. Such emitters have no internal taper (as opposed to pulled glass emitters) and therefore do not block frequently. Some embodiments of the present invention preferably use polished fused silica glass emitters than have an outer diameter between 100 µm and 500 µm and an inner diameter between 2 µm and 100 µm.

The invention claimed is:

1. An integrated system for liquid separation and electrospray ionization comprising:
   a separation column;
   an electrospray emitter connected with the separation column; and
   a retractable protective sleeve for covering and/or supporting the electrospray emitter along at least a portion of its axis, the protective sleeve is slidably mounted around the electrospray emitter;
   wherein the retractable protective sleeve is moveable to an extended position wherein a tip of the electrospray emitter is covered by the protective sleeve, and wherein a resilient member is provided to bias the protective sleeve towards the extended position wherein it covers the tip of the electrospray emitter, the protective sleeve being enclosed and moveable within an outer electrically conducting sheath adapted for insertion within a holder having a high-voltage contact point, the electrically conducting sheath being adapted to contact the high-voltage contact point and provide an electrical connection to enable the electrospray emitter to receive a high voltage and wherein the electrically conductive sheath has a recess to receive the high-voltage contact point.

2. The integrated system of claim 1, wherein the retractable protective sleeve is moveable to a retracted position wherein a tip of the electrospray emitter is uncovered.

3. The integrated system according to claim 1, wherein the separation column and electrospray emitter are embedded in a plastic material.

4. The integrated system according to claim 1, wherein the separation column is connected directly or via a transferring conduit with the electrospray emitter through one or more end fittings, and the separation column, end fittings and electrospray emitter are embedded in a plastic material.

5. The integrated system according to claim 1, wherein the separation column is an LC column.

6. The integrated system according to claim 1, wherein the separation column is coiled in a loop.

7. The integrated system according to claim 1, wherein the electrospray emitter comprises a metal capillary or a glass capillary.

8. The integrated system according to claim 1, wherein the high-voltage contact point comprises an electrically conductive ball.

9. The integrated system according to claim 8, wherein the electrically conductive ball fits in the recess in the outer surface of the electrically conductive sheath, and wherein the recess is a groove.

10. The integrated system according to claim 1, wherein the holder is fixed on a mass spectrometer.

11. An integrated system for liquid separation and electrospray ionization comprising:
 a separation column;
 an electrospray emitter connected with the separation column; and
 a retractable protective sleeve for covering and/or supporting the electrospray emitter along at least a portion of its axis, the protective sleeve is slidably mounted around the electrospray emitter;
 wherein the retractable protective sleeve is moveable to an extended position wherein a tip of the electrospray emitter is covered by the protective sleeve, and wherein a resilient member is provided to bias the protective sleeve towards the extended position wherein it covers the tip of the electrospray emitter, the protective sleeve being enclosed and moveable within an outer electrically conducting sheath adapted for insertion within a holder having a high-voltage contact point, the electrically conducting sheath being adapted to contact the high-voltage contact point and provide an electrical connection to enable the electrospray emitter to receive a high voltage and wherein the high-voltage contact point comprises an electrically conductive ball.

12. The integrated system of claim 11, wherein the retractable protective sleeve is moveable to a retracted position wherein a tip of the electrospray emitter is uncovered.

13. The integrated system according to claim 11, wherein the separation column and electrospray emitter are embedded in a plastic material.

14. The integrated system according to claim 11, wherein the separation column is connected directly or via a transferring conduit with the electrospray emitter through one or more end fittings, and the separation column, end fittings and electrospray emitter are embedded in a plastic material.

15. The integrated system according to claim 11, wherein the separation column is an LC column.

16. The integrated system according to claim 11, wherein the separation column is coiled in a loop.

17. The integrated system according to claim 11, wherein the electrospray emitter comprises a metal capillary or a glass capillary.

18. The integrated system according to claim 11, wherein the electrically conductive sheath has a recess to receive the high-voltage contact point.

19. The integrated system according to claim 11, wherein the electrically conductive ball fits a groove in the outer surface of the electrically conductive sheath.

20. The integrated system according to claim 11, wherein the holder is fixed on a mass spectrometer.

* * * * *